US006528020B1

(12) United States Patent
Dai et al.

(10) Patent No.: US 6,528,020 B1
(45) Date of Patent: Mar. 4, 2003

(54) CARBON NANOTUBE DEVICES

(75) Inventors: Hongjie Dai, Sunnyvale, CA (US); Jing Kong, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/574,393

(22) Filed: May 19, 2000

Related U.S. Application Data

(62) Division of application No. 09/133,948, filed on Aug. 14, 1998, now Pat. No. 6,346,189.
(60) Provisional application No. 60/171,200, filed on Dec. 15, 1999.

(51) Int. Cl.$^7$ .............................................. G01N 27/00
(52) U.S. Cl. ..................... 422/98; 422/82.02; 422/82.03
(58) Field of Search ................................ 422/98, 81.02, 422/81.03

(56) References Cited

U.S. PATENT DOCUMENTS

| | | | |
|---|---|---|---|
| 4,495,793 A | 1/1985 | Hager | |
| 5,334,351 A | 8/1994 | Heinze | |
| 5,436,167 A | 7/1995 | Robillard | |
| 5,448,906 A | 9/1995 | Cheung | |
| 5,571,395 A | * 11/1996 | Park et al. | .................. 204/406 |
| 5,626,650 A | 5/1997 | Rodriguez et al. | |
| 5,653,951 A | 8/1997 | Rodriguez et al. | |
| 5,726,524 A | 3/1998 | Debe | |
| 5,830,326 A | * 11/1998 | Iijima et al. | ................. 204/173 |
| 5,866,434 A | 2/1999 | Massey et al. | |
| 5,872,422 A | 2/1999 | Xu | |
| 5,891,395 A | * 4/1999 | Glaunsinger et al. | .... 422/82.02 |
| 6,012,327 A | * 1/2000 | Seth et al. | ..................... 422/90 |
| 6,105,417 A | * 8/2000 | Nosaka et al. | ................ 422/88 |
| 6,162,926 A | 12/2000 | Murphy et al. | |

OTHER PUBLICATIONS

Chen, R.J. "Molecular photodesorption from single–walled carbon nanotubes" Applied Physics Letters, Oct. 2001, vol. 79, No. 14, pp. 2258–2260.
Koshio, A. et al., "In situ laser–furnace TOF mass spectrometry of C36 and the large–scale production by arc–discharge" J. Phys. Chem. B, Jul. 2000, vol. 104, pp. 7908–7913, expecially pp. 7908–7909.
Dagani, "Much Ado About Nanotubes," *C&E News*, Jan. 11, 1999, pp. 31–34.
Dai et al., "Nanotubes as Nonopobes in Scanning Probe Microscopy," *Nature*, Nov. 14, 1996, pp. 147–150.

* cited by examiner

*Primary Examiner*—Kishor Mayekar
(74) *Attorney, Agent, or Firm*—Crawford Maunn PLLC

(57) ABSTRACT

This invention provides an assembly of novel nanotube devices that can be employed in a variety of applications. In particular, the nanotube devices of the present invention provide a new class of versatile chemical and biological sensors. The present invention describes methods for growing individual nanotubes in a controlled fashion and for manipulating and integrating the nanotubes into functional devices. It further provides methods for modifying the nanotubes such that their sensitivity to a wide range of chemical and biological species can be achieved.

20 Claims, 9 Drawing Sheets

DETECTION OF THIOL VAPOR USING Au MODIFIED SINGLE TUBE

CARBON NANOTUBE DEVICES

CROSS-REFERENCE TO RELATED APPLICATIONS

This application is a divisional/continuation-in-part of copending U.S. Pat. No. 6,346,189, issued Feb. 12, 2002, which is herein incorporated by reference. This application is based on Provisional application No. 60/171,200 filed Dec. 15, 1999, which is herein incorporated by reference.

STATEMENT REGARDING FEDERALLY SPONSORED RESEARCH OR DEVELOPMENT

This invention was supported in part by grant number 9871947 awarded by the National Science Foundation. The Government has certain rights in the invention.

FIELD OF THE INVENTION

This invention relates generally to nanotube devices. More particularly, it relates to a nanotube sensors including chemical and biological sensors.

BACKGROUND ART

Sensing, chemical and biological species plays an important role in many industrial, agricultural, medical, and environmental processes. Detection of $NO_2$ gas, for example, provides a crucial measure of environmental pollution due to combustion or automotive emissions. The amount of $NH_3$ also needs to be closely monitored in industrial, medical and living environments. Moreover, there is a growing need to detect biological species in a variety of biomedical applications.

Chemical sensors in the prior art commonly employ solid state materials, such as semiconducting metal oxides, as sensing agents. The sensing is achieved by detecting change in electrical resistance of the sensor resulted from adsorption of foreign chemical species onto the sensing material. In order to achieve significant sensitivity, however, sensors of this type must operate at elevated temperatures so to enhance chemical reactivity. Other drawbacks of these prior art sensors include long recovery times (if not rendering irreversibility), poor reproducibility, and very limited range of chemical species each sensor is able to detect.

In view of the above, there is a need in the art for sensing devices that provide not only significant and robust, but more advantageously, tunable response to a variety of chemical and biological species.

SUMMARY OF THE INVENTION

The present invention is directed to versatile nanotube devices that are adapted for use in a variety of applications. In one example embodiment of the present invention, these nanotube devices are used in chemical and biological sensors. In another example embodiment of the present invention, individually separable nanotubes are grown in a controlled fashion. In another example embodiment of the present invention, nanotubes are manipulated and integrated into functional devices such as electrical, mechanical and electrochemical devices that can be individually tailored to a wide range of applications. In still another example embodiment of the present invention, nanotubes are modified so as to tune their sensitivity to a variety of molecular and/or biological species. Devices N which these nanotubes are used demonstrate significant and robust response.

A primary advantage of certain implementations of the present invention is that it provides a new class of electrical, mechanical, and electrochemical nanotube devices that can be individually tailored to a wide range of applications. Another aspect of the present invention involves implementations of the nanotube devices demonstrating significant and robust response, and more significantly, tunable selectivity to chemical or biologal species in their environments.

These and other advantages of various embodiments of the present invention will become more evident after consideration of the ensuing description and the accompanying drawings.

According to another example embodiment of the present invention, a device comprises a substrate and two catalyst islands disposed on the substrate. Each catalyst island is capable of growing nanotubes when exposed to a hydrocarbon gas at elevated temperatures. At least one nanotube forms between, with its two ends rooted in, the two opposing islands. Metal electrodes are then placed to fully cover the catalyst islands and the two ends of the bridging nanotube, providing means for measuring electrical response of the nanotube.

The substrate is typically made of doped silicon with a layer of native oxide. The catalyst comprises $Fe_2O_3$ and alumina nanoparticles. The catalytic island is typically about 3–5 microns in size. The nanotube is generally a single-walled carbon nanotube that can be semiconducting, or metallic. The metal electrodes typically comprise an alloy of nickel-gold, or titanium-gold.

The nanotube thus produced can be further modified by coating or decorating it with one or more sensing agents, such as metal particles, polymers, and biological species which impart sensitivity to a particular molecular species.

The selectivity of the nanotube to chemical species can also be tuned physically, for example, by applying a gating voltage to a nanotube. The gating voltage effectively shifts the Fermi energy level of the nanotube, giving rise to change in electrical conductivity of the nanotube upon adsorption of foreign chemical species.

In another example embodiment of the present invention, a device comprises a substrate covered with a layer of catalyst material. The catalyst enables the growth of nanotubes when exposed to a hydrocarbon gas at elevated temperatures, yielding a film of interconnected nanotubes disposed on the substrate. Two metal electrodes are then deposited onto the two opposing sides of the film, separated by a gap devoid of any metal. Such a nanotube film device can be easily produced in a scaled-up fashion with low cost.

The substrate in the above nanotube film device is typically made of quartz. The catalyst comprises $Fe_2O_3$ and alumina nanoparticles. The nanotubes are generally single-walled carbon nanotubes that are semiconducting, or metallic. The metal electrodes typically comprise an alloy of nickel-gold, or titanium-gold.

The nanotube film may further be modified by coating or decorating it with one or more sensing agents, so as to impart sensitivity to a particular species in its environment. The sensing agents include metal particles, polymers, and biological species.

The nanotube devices of the present invention demonstrate high sensitivity, robust response, and a tunable selectivity to a wide range of molecular species. They operate in gaseous and liquid environments.

The above summary of the present invention is not intended to describe each illustrated embodiment or every implementation of the present invention. The figures and detailed description that follow more particularly exemplify these embodiments.

Figure 1A:
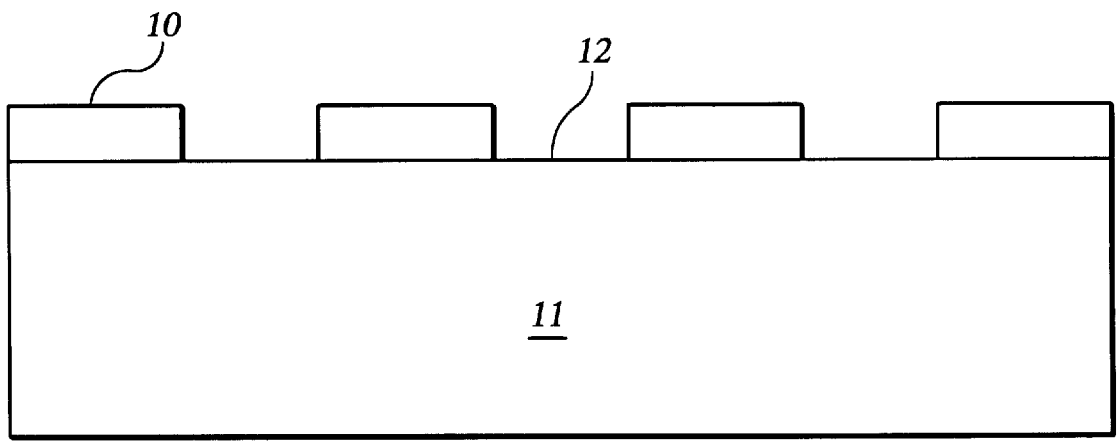
FIGS. 1A–1C depict a method for synthesizing individually distinct nanotubes on a substrate according to an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE INVENTION

Figure 1B:
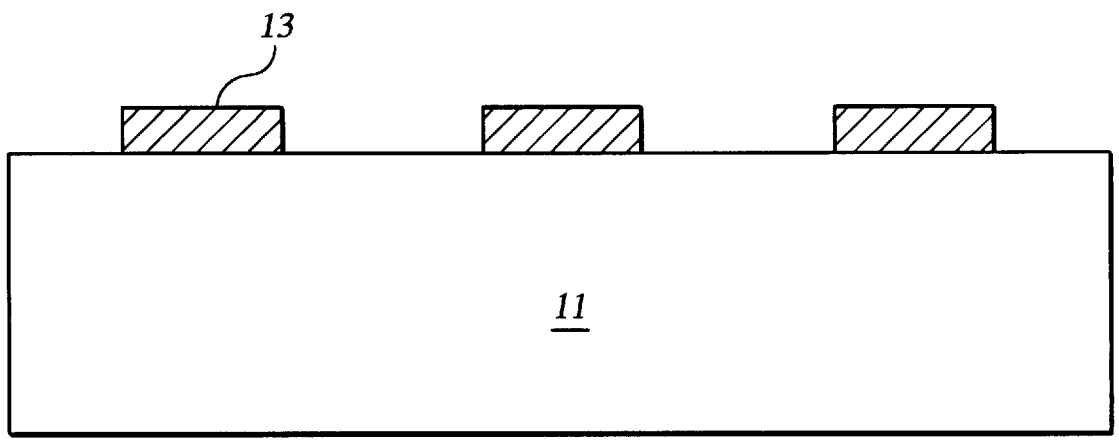
Figure 1C:
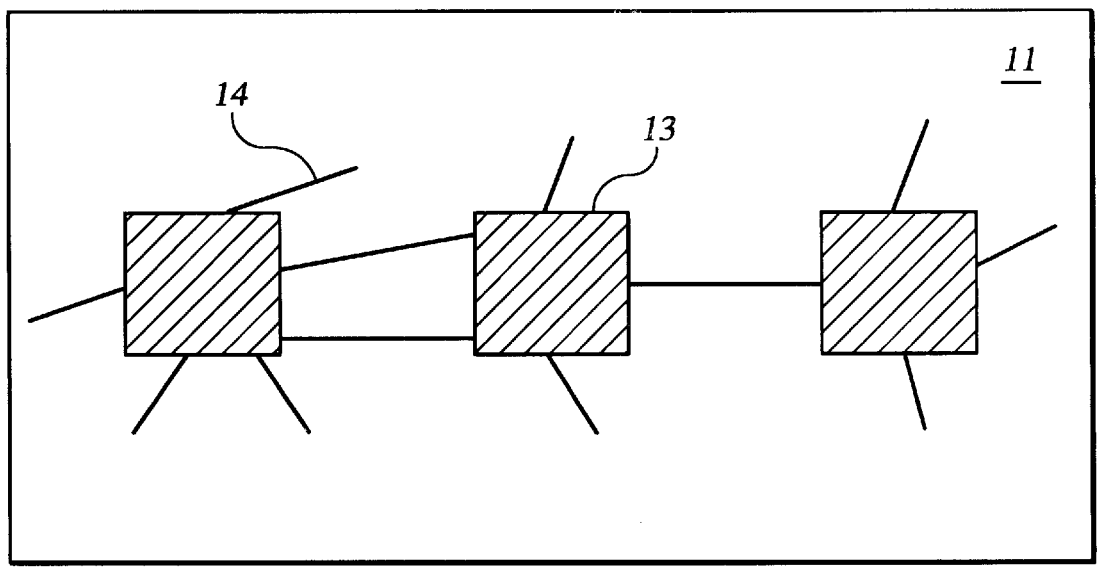

FIGS. 1A–1C illustrate a method for synthesizing individually distinct nanotubes on a silicon substrate that is patterned with catalyst islands according to a first embodiment of the present invention. The principle procedures of the method have been reported in the art by the inventors (Nature 395, 878 (1998)), incorporated herein by reference. First, a layer of resist 10 is disposed and patterned on a top surface of a substrate 11, as illustrated in FIG. 1A. The substrate 11 is made of doped silicon with a layer of native oxide. Patterning on the resist 10 is typically performed by electron-beam lithography, producing holes 12 that expose the underlying substrate 11. The holes 12 are typically 5 microns in size, spaced at a distance of 10 microns apart. Next, a few drops of a catalyst material are placed on the surface of the substrate 11, filling the holes 12. The catalyst preparation includes mixing 15 mg of alumina nanoparticles, 0.05 mmol of $Fe(NO_3)_3 9H_2O$, and 0.015 mmol of $MoO_2(acac)_2$ in 15 ml of methanol. After the solvent (i.e., methanol) dries, the remaining resist is lifted off, revealing an array of isolated catalyst islands 13 on the substrate 11, as shown in FIG. 1B. The catalyst-patterned substrate is then heated in a tube furnace to above 900° C. while exposed to a flow of methane. Heating decomposes $Fe(NO_3)_3$ to $Fe_2O_3$. The $Fe_2O_3$/nanoparticles mixture is capable of catalyzing the growth of carbon nanotubes when exposed to methane gas at elevated temperatures. The carbon nanotubes thus grown are predominantly individually distinct, single-walled nanotubes with few structural defects. FIG. 1C shows these nanotubes 14 emanated from the catalyst islands 13 on the substrate 11. They are found to be substantially straight, typically extending up to more than 10 microns in length with diameters ranging from 1–3 nanometers. Moreover, a number of the nanotubes are bridging adjacent islands. A nanotube bridge forms when a tube growing from one catalyst island falls on and interacts with another island during the synthesis process as described.

In general, the substrate can be made of a material selected from a group consisting of silicon, alumina, quartz, silica and silicon nitride. The catalyst islands comprise a material selected from a group including iron, molybdenum, cobalt, nickel, ruthenium, zinc and oxides thereof. The nanotubes can be semiconducting, or metallic.

In addition to carbon, nanotubes made of other materials (e.g., silicon) can also be grown by following a synthesis process similar to what is described above. Those skilled in the art will be able to implement the corresponding synthesis procedures.

Figure 2:
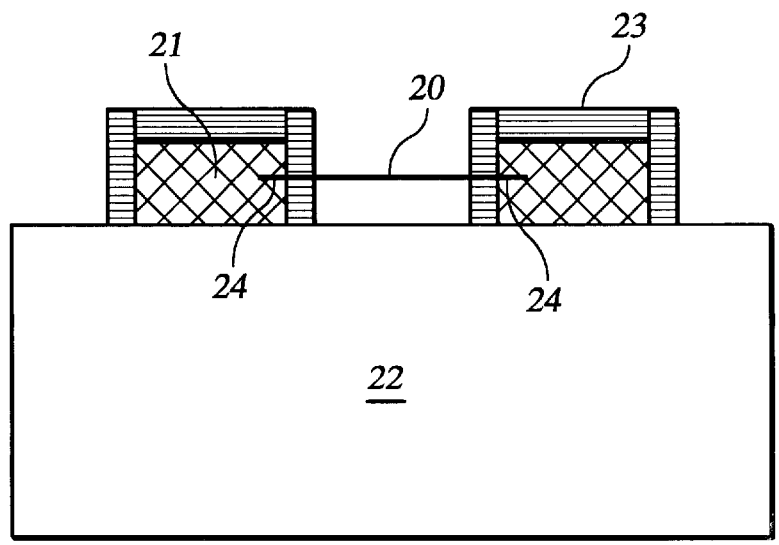
FIG. 2 illustrates an exemplary embodiment of a nanotube device comprising a single nanotube according to another example embodiment of the present invention.

The nanotube chip thus produced can be incorporated into a variety of electronic and mechanical devices. A device comprising a single nanotube can also be readily made. In one particular implementation, nanotubes bridging two catalyst islands are cut mechanically or electrically until a single tube remains using an AFM (atomic force microscopy) tip. Electron-beam lithography is then employed to deposit metal electrodes onto the two catalyst islands bridged by the nanotube. The electrodes are typically made of an alloy of nickel-gold, or titanium-gold. For example, they can be 20 nanometers of nickel with 60 nanometers gold on top. These electrodes provide electrical connections between the nanotube and macroscopic electronic circuits. FIG. 2 shows an exemplary embodiment of a nanotube device comprising a single nanotube 20 disposed between two catalyst islands 21 on a substrate 22. Two metal electrodes 23 are made to fully cover respective catalyst islands 21. including the two ends 24 of the bridging nanotube 20.

Figure 3A:
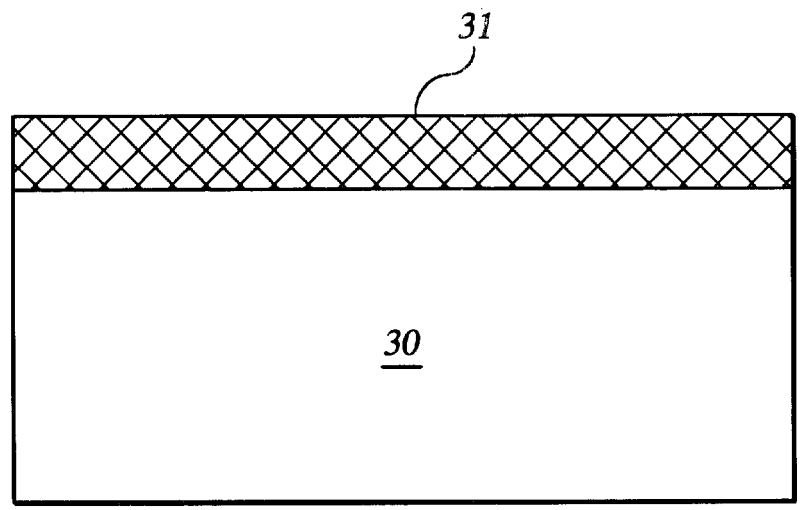
FIGS. 3A–3B show a method for making a nanotube film device according another example embodiment of the present invention.
Figure 3B:
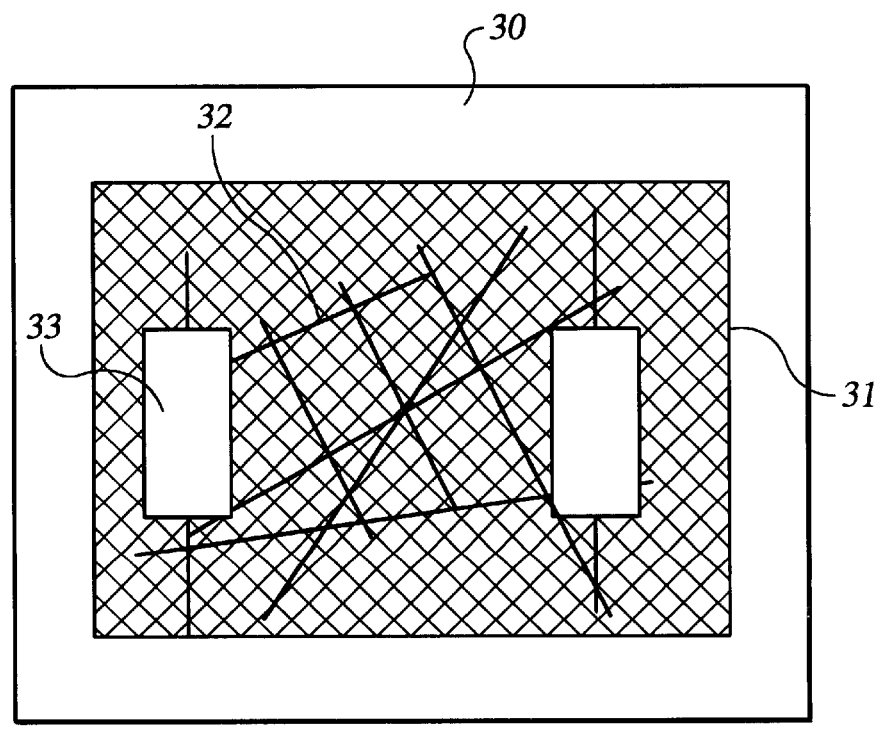

FIGS. 3A–3B show a method for synthesizing a film of nanotubes on a substrate that is initially covered with a layer of catalyst according to a second embodiment of the present invention. First, a quartz substrate 30 is coated with a layer of catalyst 31 by spin-coating, as shown in FIG. 3A. The catalyst is typically prepared by mixing 15 mg of alumina nanoparticles, 0.05 mmol of $Fe(NO_3)_3 9H_2O$, and 0.015 mmol of $MoO_2(acac)_2$ in 15 ml of methanol. The catalyst-covered substrate is then heated to above 900° C. in a flow of methane, yielding a film of interconnected single-walled carbon nanotubes 32 on the substrate, as shown in FIG. 3B. Two metal electrodes 33, each comprising 20 nanometers of titanium followed by 60 nanometers of gold, are then evaporated onto the nanotube film through a shadow mask, such that there is a metal-free gap forming between the two electrodes 33. Such a nanotube film device can be easily produced in a scaled-up fashion with low cost.

The substrate in FIGS. 3A–3B is typically made of a material selected from a group consisting of silicon, alumina, quartz, silica and silicon nitride. The catalyst islands comprise a material selected from a group including iron, molybdenum, cobalt, nickel, ruthenium, zinc and oxides thereof. The nanotubes can be semiconducting, or metallic. The electrodes are typically made of an alloy of nickel-gold, or titanium-gold.

The nanotube devices described above can be further physically or chemically modified, so as to be tailored for a particular application. A semiconducting or metallic carbon nanotube exhibits inherent change in electrical conductance when exposed to certain chemical gases, resulted from adsorption of the gas particles on the nanotube. More significantly, by depositing one or more sensing agents onto the nanotube, its sensitivity to a wide range of chemical and biological species can be achieved. The selectivity of the nanotube to chemical species call be also tuned by applying a gating voltage to the nanotube. The gating voltage effectively shifts the Fermi energy level of the nanotube, enabling the nanotube to be more responsive to a particular species. In one particular implementation, a gating voltage in the range of about −20 to 20 volts is applied to the nanotube. The embodiments described hereinafter demonstrate the functionality and versatility of the novel nanotube devices of the present invention.

Figure 4:
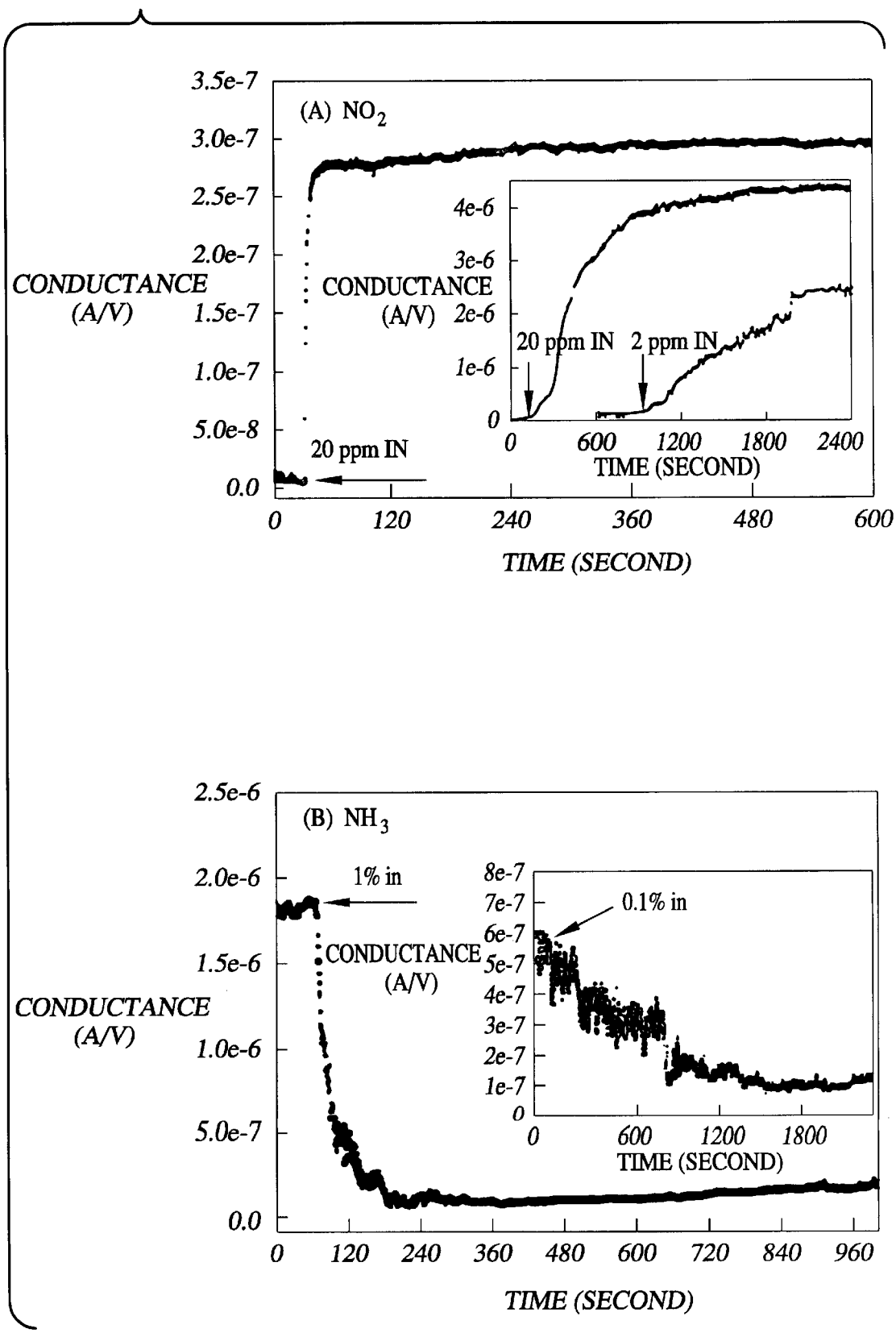
FIG. 4 displays electrical response of a single nanotube device to NO2 and NH3, respectively, according to another example embodiment of the present invention.

FIG. 4 displays electrical responses of a device comprising a semiconducting single-walled carbon nanotube to various amounts of $NO_2$ and $NH_3$ gas, respectively. The gas sensing is carried out by enclosing the device in a glass flask. The flask is equipped with electrical feedthrough that makes electrical connections between the device and the electrical measurement circuits on the outside. It also permits a flow of gas. A carrier gas (e.g., Ar or air), diluted with $NO_2$ or $NH_3$, then flows through the flask, while the electrical response of the nanotube is recorded. The device displays fast and significant response to the arrival of $NO_2$ and $NH_3$, respectively. Moreover, after each gas sensing measurement, the electrical characteristics of the nanotube is able to fully recover in a flow of pure carrier gas over a period of several hours.

Figure 5:
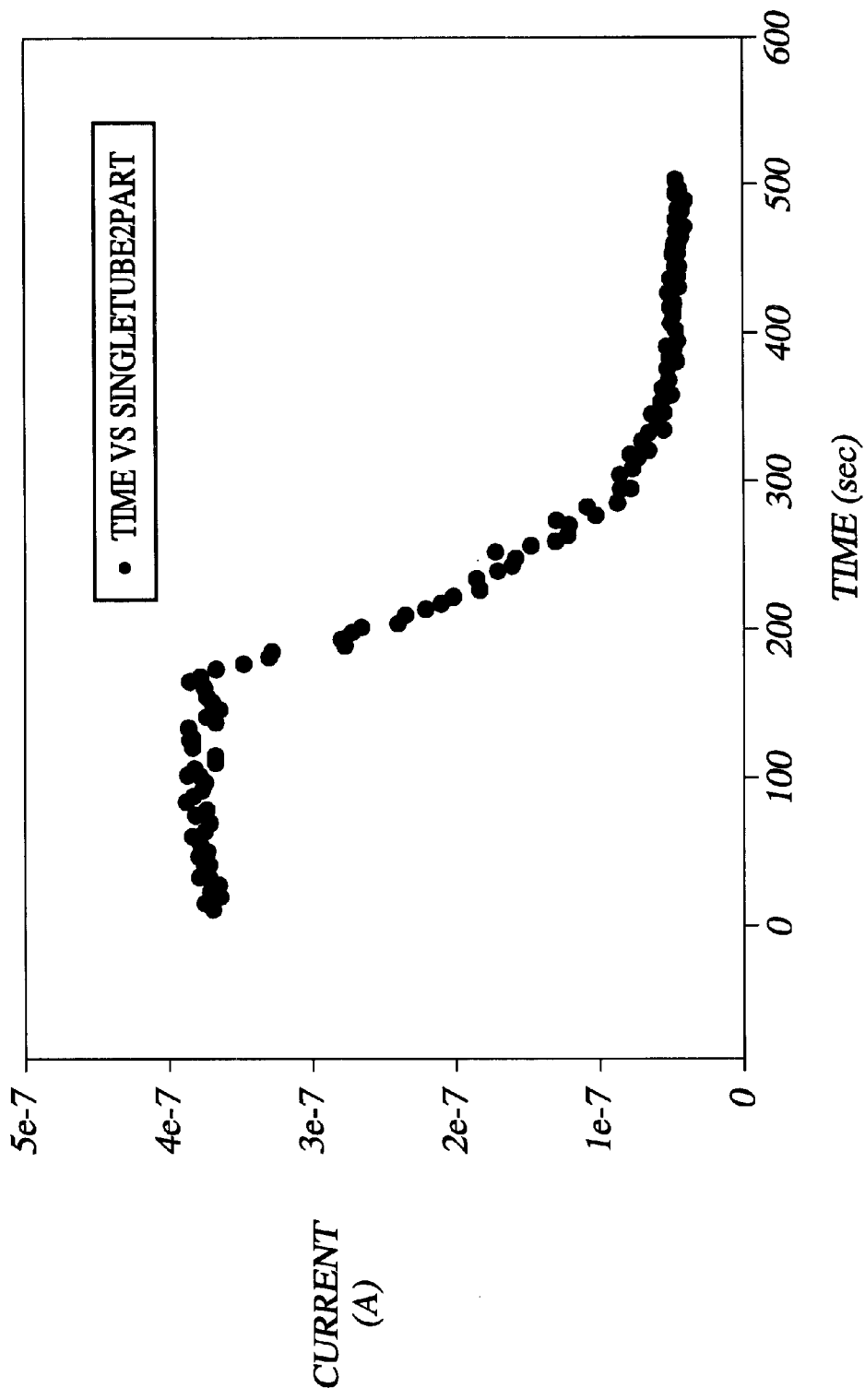
FIG. 5 shows electrical response of a gold-decorated single nanotube device to thiol vapor, according to another example embodiment of the present invention.

FIG. 5 shows electrical response of a gold-decorated single nanotube to thiol vapor. Gold is deposited on the nanotube by evaporation. Since it does not wet carbon, the evaporated gold particles decorate, rather than forming a continuous layer on the nanotube. The observed response to thiol results from the presence of the gold particles in this case, since the carbon nanotube alone does not respond to thiol. Given that many biological molecules like to link themselves onto thiol, by attaching a layer of thiol to a gold-decorated nanotube, this composite system promises to be a versatile biological sensor.

Figure 6:
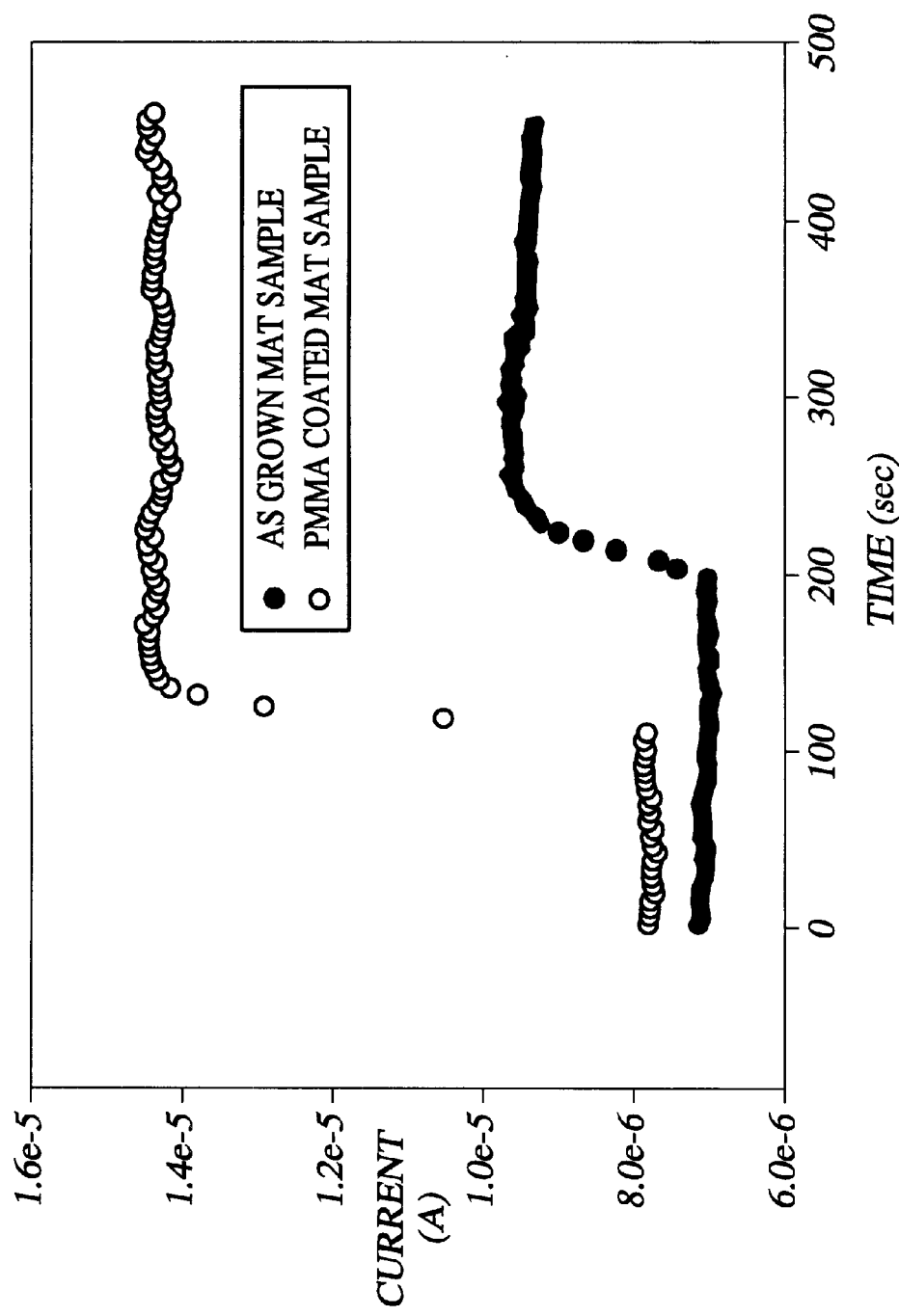
FIG. 6 displays electrical responses of an as-grown nanotube film device and a PMMA-coated nanotube film device to NO2 gas, according to another example embodiment of the present invention.

FIG. 6 shows electrical responses of an as-grown nanotube film (mat) device and a PMMA (polymethylmethacrylate)-covered nanotube film (mat) device to $NO_2$ gas. The PMMA coating in the later case is typically about 100 nanometers thick, and its presence significantly improves the sensitivity and the response time of the nanotube device to $NO_2$.

Figure 7A:
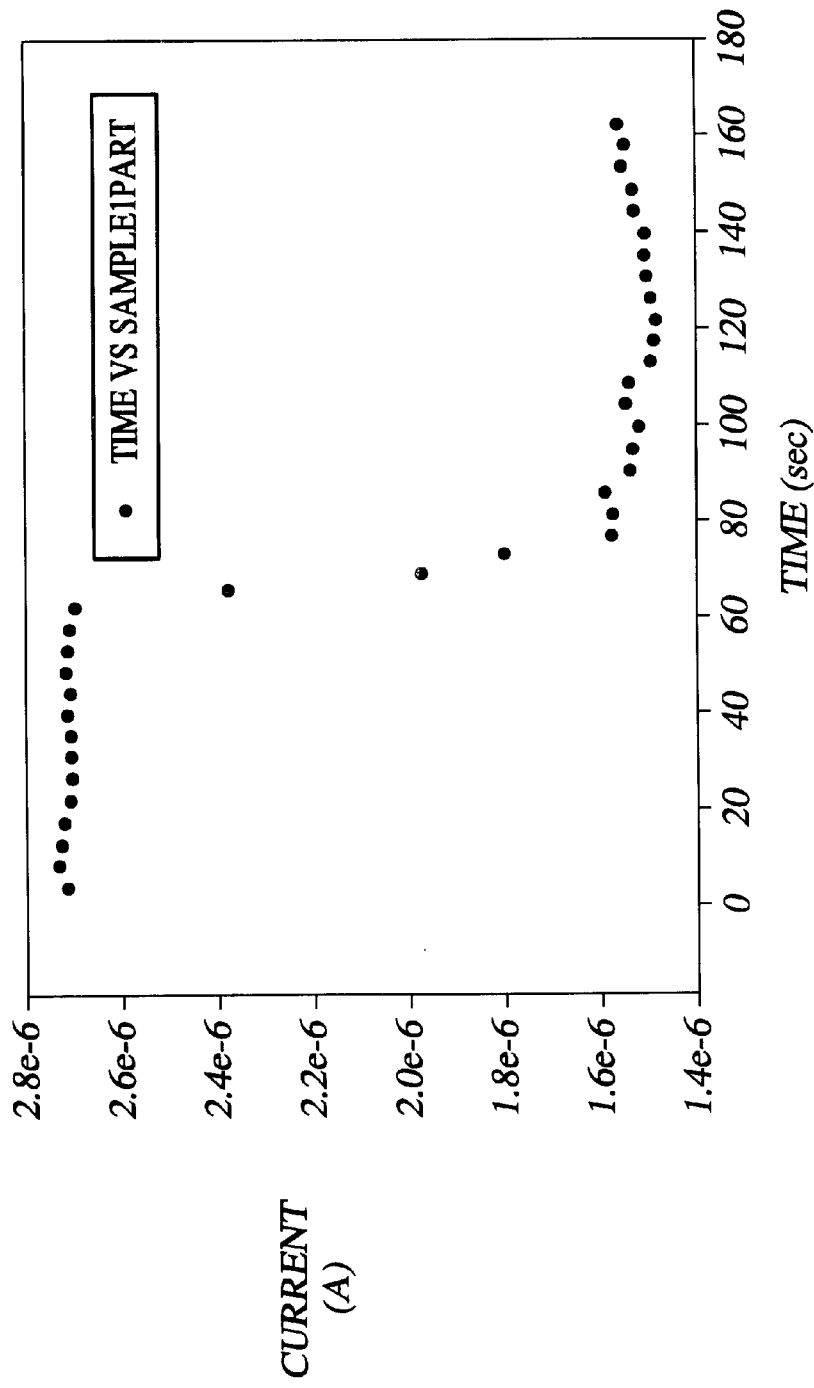
FIGS. 7A–7B show electrical response of a gold-decorated nanotube film device to thiol vapor and the detection of avidin using a thiol-coated-gold-decorated nanotube film device, according to another example embodiment of the present invention.
Figure 7B:
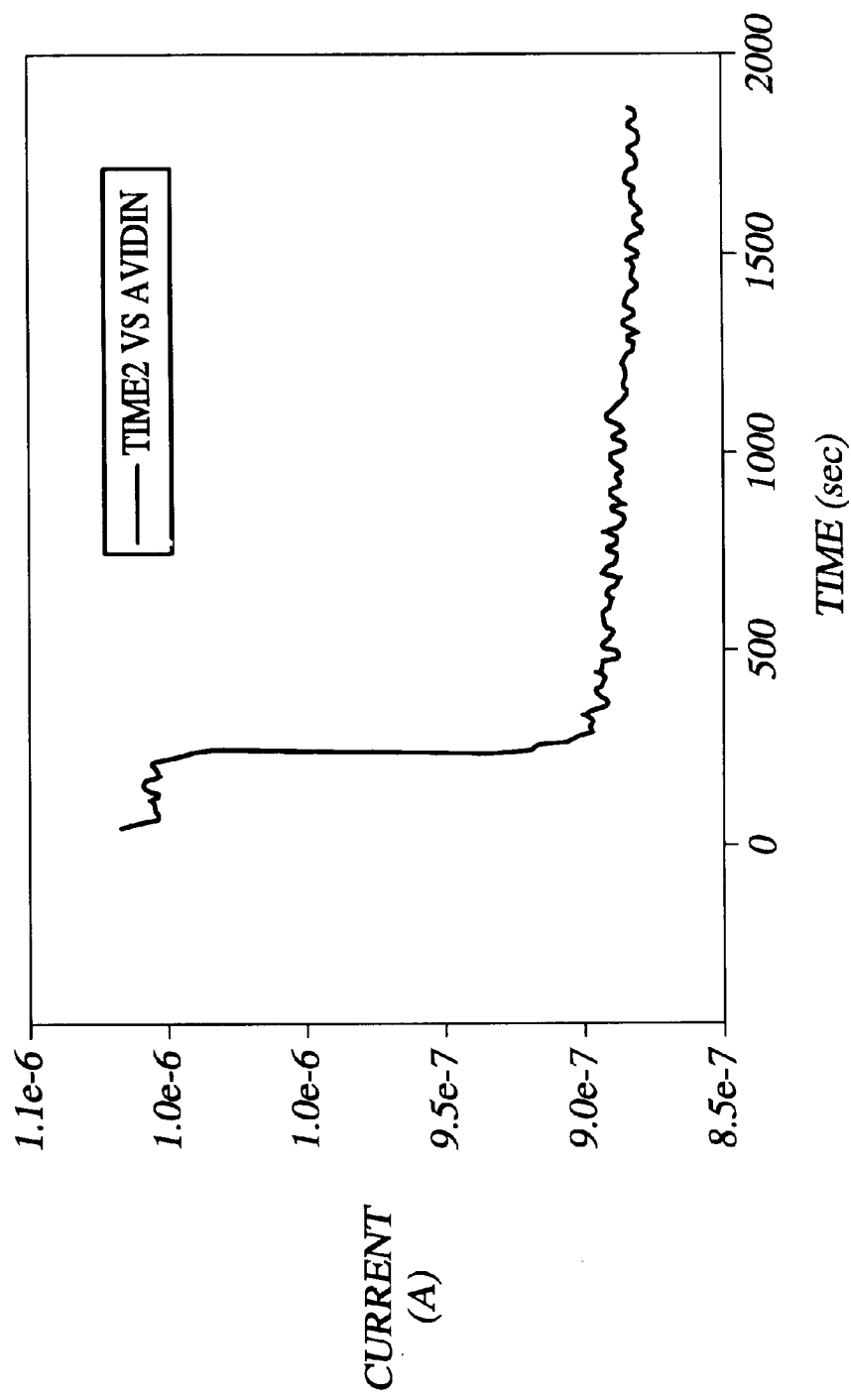

FIG. 7A displays electrical response of a gold-decorated nanotube film device to thiol vapor, and FIG. 7B shows the detection of avidin (a protein) using a thiol-coated-gold-decorated film device. In this case, gold particles are first evaporated onto the nanotube film, followed by attaching a monolayer of thiol with carboxylic functional group to the gold particles. The presence of thiol modifies the electrical conductance of the nanotube device. When exposed to avidin, the carboxylic groups of the thiol molecules like to be linked to avidin molecules via carbodimide chemistry, giving rise to further change in electrical conductance of the nanotube film device. Note that in this case, the nanotube device operates in a liquid environment.

Figure 8:
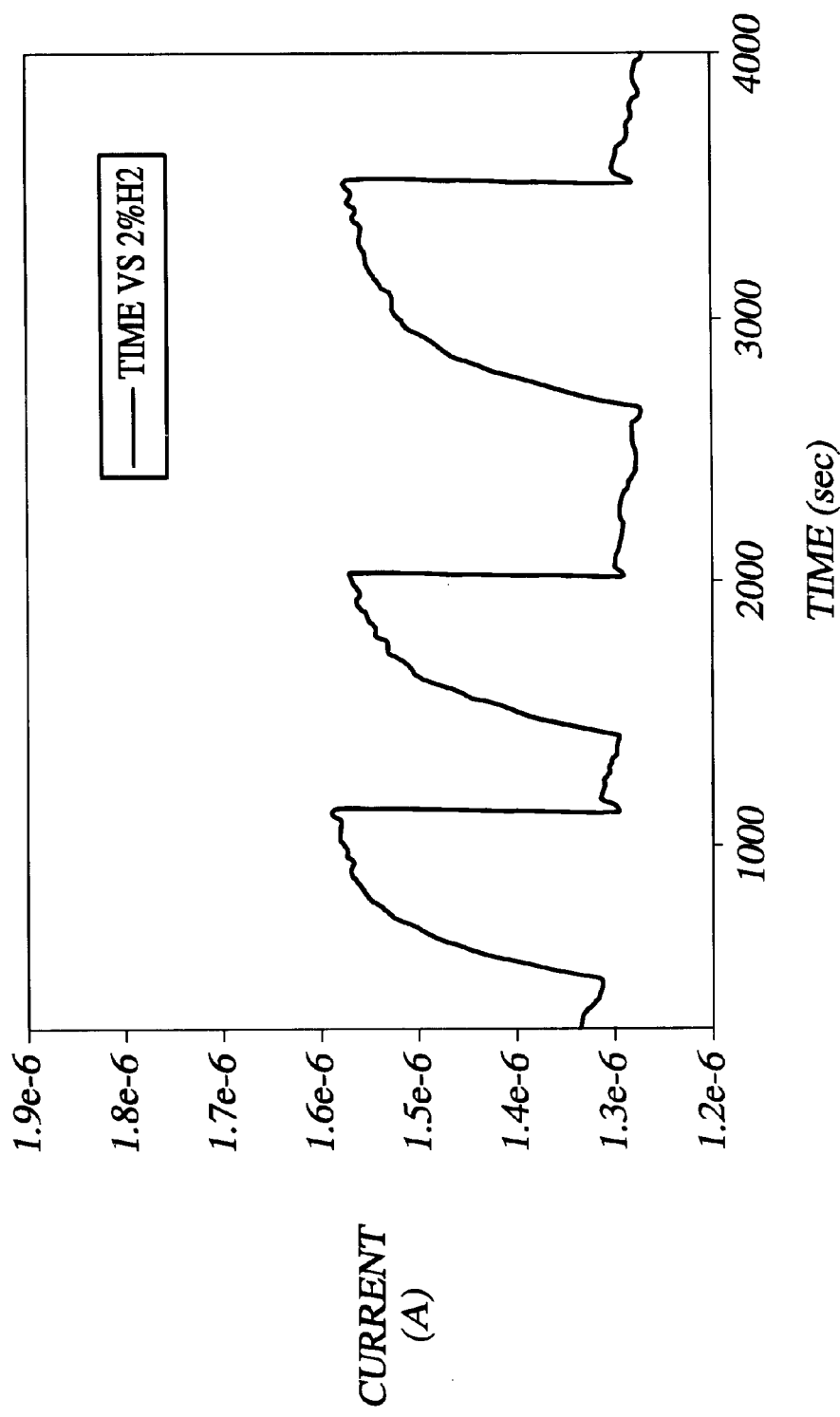
FIG. 8 displays the detection of H2 using a platinum-modified nanotube film device, according to another example embodiment of the present invention.

FIG. 8 shows the detection of $H_2$ using a platinum-modified nanotube film device. Platinum particles are deposited onto and decorate the nanotubes film. It is their presence that enables the device to respond to $H_2$ molecules.

Moreover, by attaching an enzyme to a nanotube or a nanotube film, the corresponding enzyme-coated nanotube device displays changes in its electrical conductance when exposed to glucose, and other biological species. This would have important implications in medicine. Sensing CO has also been achieved by using modified nanotube devices.

In additional to the sensing agents described above, other metal particles (e.g., nickel, rhodium, palladium, and $TiO_2$), polymers, and biological species can be used as sensing agents to modify the sensitivity of nanotubes to chemical and biological species.

Clearly, the capabilities of the nanotube devices of the present invention as chemical and biological sensors are not merely limited to the exemplary embodiments described above. Furthermore, the nanotube devices of the present invention can be utilized as electrochemical, electromechanical and other functional devices.

While the present invention has been described with reference to several particular example embodiments, those skilled in the art will recognize that many changes may be made thereto. Such changes and implementations do not depart from the spirit and scope of the present invention, which is set forth in the following claims.

What is claimed is:

1. A molecular sensor comprising:
   a) a nanotube device comprising at least one carbon nanotube, wherein a first end of said nanotube is in electrical contact with a first conducting element and a second end of said nanotube is in electrical contact with a second conducting element; and
   b) a coating of one or more sensing agents deposited on said nanotube;

wherein said sensing agents are so chosen such that the agents-coated nanotube responds to a particular molecular species.

2. The molecular sensor of claim 1 wherein said one or more sensing agents comprise one or more materials selected from the group consisting of metal particles, polymers, and biological species.

3. The molecular sensor of claim 2 wherein said group includes gold, platinum, nickel, rhodium, palladium, $TiO_2$, thiol, and enzymes.

4. The molecular sensor of claim 1 wherein said nanotube is semiconducting.

5. The molecular sensor of claim 4 further comprising a voltage source applying a gating voltage to said nanotube, wherein said gating voltage is so chosen such that said nanotube biased with said gating voltage responds to a particular molecular species.

6. The molecular sensor of claim 5 wherein said gating voltage is typically in the range of −20 to 20 Volts.

7. A sensing method comprising the steps of:
   a) disposing a molecular sensor comprising at least one carbon nanotube inside an enclosure, wherein a first end of said nanotube is in electrical contact with a first conducting element and a second end of said nanotube is in electrical contact with a second conducting element;
   b) connecting said first and second conducting elements to an electrical measurement circuit; and
   c) introducing a molecular species to said enclosure, while monitoring, an electrical response of said molecular sensor.

8. The sensing method of claim 7 wherein said molecular species comprises a gas.

9. The sensing method of claim 7 wherein said molecular species comprises a liquid.

10. The sensing method of claim 7 further comprising depositing one or more sensing agents on the nanotube so to enable said nanotube to respond to said molecular species.

11. The sensing method of claim 10, wherein depositing one or more sensing agents includes modifying an electrical characteristic of the carbon nanotube.

12. The sensing method of claim 11, wherein modifying an electrical characteristic of the carbon nanotube includes modifying the electrical conductance of the carbon nanotube.

13. The sensing method of claim 10, wherein depositing one or more sensing agents includes depositing an enzyme that causes an electrical characteristic of the carbon nanotube to change in response to a biological species being introduced to the enzyme coated carbon nanotube.

14. The sensing method of claim 10, wherein depositing one or more sensing agents includes depositing one or more materials selected from the group consisting of metal particles, polymers, and biological species.

15. The sensing method of claim 7 wherein said nanotube is semiconducting, and wherein said nanotube is biased with a gating voltage so to enable said nanotube to respond to said molecular species.

16. The sensing method of claim 7, wherein introducing a molecular species to said enclosure includes flowing a carrier gas with the molecular species into the enclosure.

17. The sensing method of claim 7, further comprising using the monitored electrical response to detect a characteristic of the molecular species.

18. A molecular sensor comprising at least one carbon nanotube having been treated with a sensing agent, the sensing agent being configured and arranged to cause the nanotube to electrically respond to a particular molecular species.

19. The molecular sensor of claim 12, wherein a first end of the nanotube is in electrical contact with a first conducting element and a second end of the nanotube is in electrical contact with a second conducting element and wherein the first and second conducting elements are adapted for detecting the electrical response of the carbon nanotube.

20. The molecular sensor of claim 18, wherein the sensing agent is adapted to attach to molecules and wherein the carbon nanotube is adapted to electrically respond to the attached molecules, the molecular sensor being adapted to detect the presence of the attached molecules via an electrical response of the carbon nanotube.

* * * * *

UNITED STATES PATENT AND TRADEMARK OFFICE
CERTIFICATE OF CORRECTION

PATENT NO.     : 6,528,020 B1
DATED          : March 4, 2003
INVENTOR(S)    : Dai et al.

It is certified that error appears in the above-identified patent and that said Letters Patent is hereby corrected as shown below:

Column 1,
Line 64, "Devices N" should read -- Devices in --.

Column 8,
Line 11, "sensor of claim 12" should read -- sensor of claim 18 --.

Signed and Sealed this

Twelfth Day of August, 2003

JAMES E. ROGAN
*Director of the United States Patent and Trademark Office*